(12) United States Patent
Page et al.

(10) Patent No.: US 12,247,199 B2
(45) Date of Patent: *Mar. 11, 2025

(54) NUCLEIC ACID ELUTION

(71) Applicant: Global Life Sciences Solutions USA LLC, Marlborough, MA (US)

(72) Inventors: Andrew Francis Page, Wilmington, DE (US); Breck Olland Parker, Sanford, ME (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/340,609

(22) Filed: Jun. 23, 2023

(65) Prior Publication Data

US 2023/0332133 A1  Oct. 19, 2023

Related U.S. Application Data

(62) Division of application No. 17/122,606, filed on Dec. 15, 2020, now Pat. No. 11,725,201, which is a division of application No. 13/519,391, filed as application No. PCT/EP2010/070389 on Dec. 21, 2010, now abandoned.

(60) Provisional application No. 61/290,652, filed on Dec. 29, 2009.

(51) Int. Cl.
*C12N 15/10* (2006.01)
*C12Q 1/6806* (2018.01)

(52) U.S. Cl.
CPC ....... *C12N 15/1003* (2013.01); *C12Q 1/6806* (2013.01)

(58) Field of Classification Search
CPC .......................... C12N 15/1003; C12Q 1/6806
USPC ....................................................... 536/25.4
See application file for complete search history.

(56) References Cited

U.S. PATENT DOCUMENTS

| 5,496,562 | A | 3/1996 | Burgoyne | |
| 11,725,201 | B2* | 8/2023 | Page | C12Q 1/6806 |
| | | | | 536/25.4 |
| 2003/0092045 | A1 | 5/2003 | Nargessi | |
| 2003/0166594 | A1 | 9/2003 | Blum | |
| 2004/0033546 | A1* | 2/2004 | Wang | G01N 33/5308 |
| | | | | 435/287.2 |
| 2005/0090009 | A1* | 4/2005 | Cormier | A61K 48/0025 |
| | | | | 435/459 |
| 2006/0153920 | A1 | 7/2006 | Amin et al. | |

FOREIGN PATENT DOCUMENTS

| WO | 2003/016552 A2 | 2/2003 |
| WO | 2003/044211 A2 | 5/2003 |
| WO | 2005/042702 A2 | 5/2005 |

OTHER PUBLICATIONS

Su et al. Cellulose as a Matrix for Nucleic Acid Purification. Analytical Biochemistry 267, 418-420 (1999). (Year: 1999).*
European Office Action for EP Application No. 10 796 044.5 mailed Feb. 26, 2015 (4 pages).
Dejonge, J., et al., European Journal of Pharmaceutical Sciences, vol. 32, pp. 33-44. (year: 2007).
CN Search Report Dated Feb. 10, 2014 Issued on Corresponding Chinese Patent Application No. 201080059859.X.
Hinrichs, W., et al., Journal of Controlled Release, 103 (2005) 465-479.
Hinrichs, W., et al., International Journal of Pharmaceutics, 311 (2006) 237-244.
Makowski, et al., Journal of Clinical Laboratory Analysis 11:87-93 (1997).

* cited by examiner

*Primary Examiner* — Yih-Horng Shiao
(74) *Attorney, Agent, or Firm* — Eversheds-Sutherland (US) LLP

(57) ABSTRACT

This invention relates to the storage on a solid matrix of genetic material, in particular DNA that has been purified prior to the application to the solid matrix. More specifically, the invention relates to a solid matrix for the storage of purified DNA, which matrix has been treated with a solution comprising plant polysaccharide inulin. One advantage of the invention is that an increased amount of DNA can be stored in the solid matrix of the present invention."

14 Claims, 1 Drawing Sheet

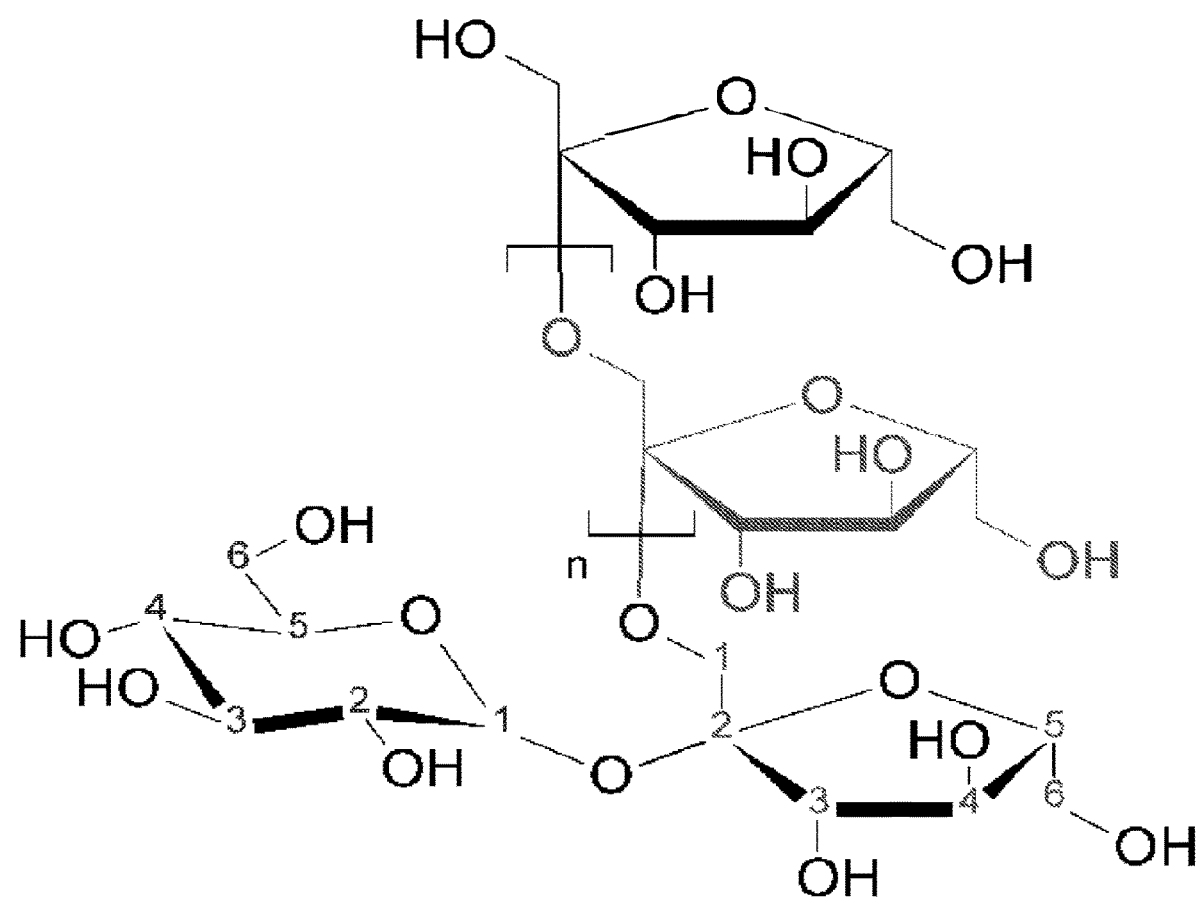

NUCLEIC ACID ELUTION

CROSS REFERENCE TO RELATED APPLICATIONS

This application is a divisional application of U.S. application Ser. No. 17/122,606, filed Dec. 15, 2020, which is a divisional application of U.S. application Ser. No. 13/519,391, filed Jun. 27, 2012, abandoned, which claims the priority benefit of PCT/EP2010/070389, filed Dec. 21, 2010, which claims the priority benefit of U.S. Provisional Application No. 61/290,652, filed Dec. 29, 2009. The content of these applications is incorporated by reference herein.

FIELD OF THE INVENTION

This invention relates to the storage on a solid matrix of genetic material, in particular DNA that has been purified prior to the application to the solid matrix.

BACKGROUND OF THE INVENTION

Storing of nucleic acids, particularly DNA, is typically accomplished in solution using refrigeration either at 4° C. for up to several days or −20° C. or even lower temperatures for longer periods. This is costly and space consuming for static storage. It presents greater issues when nucleic acid samples require transportation and samples are often shipped in dry ice.

Burgoyne (WO 90/03959) described a method whereby biological samples, usually blood, could be applied to a solid matrix which combined reagents which lysed the cells. The released DNA was retained on the solid matrix. These samples could be stored for long periods at room temperature.

U.S. Pat. No. 5,939,259 and WO 03/016552 describe techniques whereby the DNA associated with the solid matrix could be eluted for further study. In many cases however, recovery of the purified DNA applied to the solid matrix results in about 40% of the DNA recovered as determined by quantitative real time PCR. There is clearly a need for a simple method which stores DNA at room temperature for long periods of time but allows greater recovery of the applied DNA.

SUMMARY OF THE INVENTION

It has been surprisingly observed that the addition of inulin (a polysaccharide found in plants) to the solid matrix, greatly increases the percentage of the applied DNA that can be eluted from the solid matrix. This is particularly apparent when purified DNA is applied the solid matrix.

BRIEF DESCRIPTION OF THE DRAWINGS

FIG. 1 shows the structure of inulin.

DETAILED DESCRIPTION OF THE INVENTION

A range of chemicals was added to a solid matrix to study their effect on the yields of DNA recovered from the solid matrix. In particular the solid matrix known as FTA Elute (Whatman) has proved to be particularly useful in the practice of the current invention. However, it is anticipated that other types of solid matrix can also be used with the invention. Many of the solid matrices are based on cellulose. The solid matrix was treated with a solution of test reagents diluted in 2M guanidine isothiocynate. Many chemicals had little or no effect on the yield of DNA recovered. Polyethylene glycol (PEG) at concentrations of about 10% had a small increase on the amount of DNA recovered. PEG is a long chain polymer of ethylene glycol subunits. PEG is prepared in a variety of molecular weights defined by the average number of subunits per molecule. Polymers of MW 400, 1000 and 3350 were evaluated. It was observed that PEG 1000 produced the best recovery of applied DNA results (data not shown) and was used in the remainder of the tests but is referred to as PEG. At concentration of PEG at about 25% the results varied between experiments; this may imply small inconsistencies in the coating process of the solid matrix at these concentrations.

It was found that when the solid matrix was treated with the plant polysaccharide inulin then increases in the amount of DNA eluted from the solid matrix was observed. It was found that adding inulin up to concentrations of 20% to the solid matrix increases the yield of DNA recovered from the solid matrix from 25-40%, without the addition of inulin to 80%. There were indications that adding 10% PEG in addition to the added inulin increased the yield of recovered DNA to approximately 85%.

Inulin is a naturally occurring polysaccharide found in many plants. Its structure is given in FIG. 1. it is anticipated that simple modifications of inulin eg esterification would be possible and still achieve the improved elution of the applied purified DNA.

The purified DNA can be applied to the solid matrix that has been treated with inulin in buffers that are routinely used in nucleic acid chemistry. Up to 10% PEG can also be included in the application buffer. The DNA prior to application to the solid matrix can be purified by a variety of standard laboratory techniques.

An important consideration is that the increased yield of recovering DNA is maintained with time ie. prolonged storage at room temperature. It has been found that DNA can be recovered with increased yield for at least twenty-three days. It is expected that this increased yield will occur with even longer storage periods. Room temperature is usually about 20°–25° C. with a typical value of 20° C.

EXAMPLES

The present example is provided for illustrative purposes only, and should not be construed as limiting the present invention as defined by the appended claims.

Example 1 Matrix Chemistry Modification

The solid matrix was FTA Elute 903 matrix from Whatman.

1) A 4 M stock of guanidine thiocyanate was prepared and diluted to 2 M using various concentrations of test reagents.
2) 903 matrix (2¼"×2¼") was placed into trays containing guanidine thiocyanate/test reagent mixes and agitated gently for 10 seconds.
3) Matrices were dried for 10 min on a metal rack using two hair dryers (Simply Basic DS-727); one placed at a 30° angle 15 cm above the matrix, the other placed 25 cm below the matrix at a 30° angle such that the two hair dryers and the matrix were in alignment. Matrices were dried further without the air flow at 21±2° C. overnight.

4) Matrices were stored at room temperature in a desiccator until use.

Example 2 Application of DNA to Test Solid Matrix

Human DNA (Roche) was spotted onto the test solid matrix at concentration of 160 ng/μl. Usually a pre-punched 5 mm diameter disc of the matrix was used. Discs were dried at room temperature for a minimum of 3 hours.

Example 3 Elution of DNA from Solid Matrix

1) Each dried disc was placed in a sterile 1.5 ml microfuge tube and washed with 500 μl dH$_2$O by pulse vortexing three times for a total of five seconds.
2) Discs were transferred to 0.5 ml microfuge tubes containing 100 μl of dH$_2$O, ensuring that discs were fully submerged.
3) Microfuge tubes were placed in a heat block for 30 min at 98° C.
4) Microfuge tubes were pulse vortexed for 60 sec and then briefly centrifuged.
5) Eluates were transferred to new 0.5 ml tubes, leaving discs behind. Eluates were stored at 4° C. until quantification.

Example 4 Quantification of DNA in Eluates

Quantification of DNA in eluates was performed by QPCR using a 7900HT Thermal Cycler (Applied Biosystems). Reactions were set up using an RNase P assay and TAQMAN® Universal PCR Master Mix (Applied Biosystems). A four point standard curve was prepared using a serial dilution from 10 to 0.01 ng/μl of the same Roche DNA used for experiments. Early QPCR quantifications were performed in 96-well plates and were set up manually. Following the introduction and validation of a liquid handling robot, later quantifications were performed using 384-well plates. Both 96 and 384-well plates were validated and also tested against each other to check for consistency between methods.

RESULTS

Results (Table 1) show that matrices impregnated with either inulin or PEG did result in increased DNA recovery compared to FTA Elute by itself In addition to this, the use of a spotting buffer containing 10% PEG resulted in an additional increase in DNA yield (85% when used with FTA Elute+20% inulin).

TABLE 1

Percent recoveries of DNA (1 μg) applied to FTA Elute matrices impregnated with additional chemicals. Spotting buffers were mixed with DNA immediately prior to application to pre-punched 5 mm diameter discs. For each entry, n = 4. Discs were dried and DNA eluted as described in section 1.1.

| | | Spotting Buffer | |
| --- | --- | --- | --- |
| | | DNA Only | 10% PEG |
| FTA Elute | 10% PEG | 49 | 66 |
| Matrix | 20% Inulin | 62 | 85 |
| | FTA Elute | 42 | 48 |

The matrix containing 20% inulin showed the highest % recovery of applied purified DNA. Since PEG was also identified as a possible additive to matrix impregnation chemistry, FTA Elute impregnated with a combination of 20% inulin and 10% PEG was also prepared for further investigation. A spotting buffer containing 10% PEG was confirmed as further increasing yields when used in conjunction with the modified matrix chemistry.

Results were also obtained from experiments where the discs with applied purified DNA had been stored in a dessicator at room temperature. The results showed that the discs could be stored for at least twenty-three days before DNA elution with similar increased recovery of DNA when the matrix had been treated with inulin.

Results also showed that the amount of DNA applied and recovered from the test matrix could be as low as 1 μg and as high as 1 μg (the maximum tested) and the increased effect on inulin treatment was still observed.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A composition for the storage of a purified nucleic acid, the composition consisting of:
   a solid matrix,
   guanidine thiocyanate,
   inulin, and optionally a purified nucleic acid, a polyethylene glycol, or a buffer;
   wherein the solid matrix is impregnated with the inulin and the guanidine thiocyanate.
2. The composition of claim 1, wherein the composition does not include the purified nucleic acid.
3. The composition of claim 1, wherein the solid matrix is impregnated with the polyethylene glycol.
4. The composition of claim 1, wherein the purified nucleic acid is stored in the solid matrix.
5. The composition of claim 4, wherein the purified nucleic acid is non-lyophilized.
6. The composition of claim 4, wherein the purified nucleic acid comprises DNA.
7. The composition of claim 6, wherein the DNA comprises human DNA.
8. The composition of claim 1, wherein the solid matrix is a cellulose-based matrix.
9. A composition for the storage of a purified nucleic acid, the composition consisting of:

a solid matrix,
inulin,
guanidine thiocyanate,
polyethylene glycol and optionally a purified nucleic acid or a buffer;
wherein the solid matrix is impregnated with the inulin, the guanidine thiocyanate, and the polyethylene glycol, and
wherein the solid matrix is a cellulose-based matrix.

10. The composition of claim 9, wherein the composition does not include the purified nucleic acid.

11. The composition of claim 9, wherein the purified nucleic acid is non-lyophilized, and wherein the non-lyophilized nucleic acid is stored in the solid matrix.

12. The composition of claim 11, wherein the purified nucleic acid comprises DNA.

13. The composition of claim 12, wherein the DNA comprises human DNA.

14. A composition for the storage of a purified nucleic acid, the composition consisting of:
a solid matrix,
inulin,
guanidine thiocyanate,
polyethylene glycol and optionally a buffer;
wherein the solid matrix is impregnated with the inulin, the guanidine thiocyanate, the polyethylene glycol and optionally the buffer,
wherein the solid matrix is a cellulose-based matrix, and
wherein the composition does not include the purified nucleic acid.

* * * * *